United States Patent
Closson et al.

(10) Patent No.: US 9,115,330 B2
(45) Date of Patent: Aug. 25, 2015

(54) DIETHYL-METHYL-HEXAHYDRO-ISOBENZOFURANS AND THEIR USE IN PERFUME COMPOSITIONS

(71) Applicants: Adam P. Closson, Jersey City, NJ (US); Ryan D. Oesterle, Jackson, NJ (US); Nicole L. Giffin, Hazlet, NJ (US); Michael G. Monteleone, Hazlet, NJ (US)

(72) Inventors: Adam P. Closson, Jersey City, NJ (US); Ryan D. Oesterle, Jackson, NJ (US); Nicole L. Giffin, Hazlet, NJ (US); Michael G. Monteleone, Hazlet, NJ (US)

(73) Assignee: International Flavors & Fragrances Inc. NY (US)

( * ) Notice: Subject to any disclaimer, the term of this patent is extended or adjusted under 35 U.S.C. 154(b) by 67 days.

(21) Appl. No.: 13/888,713

(22) Filed: May 7, 2013

(65) Prior Publication Data
US 2014/0336102 A1    Nov. 13, 2014

(51) Int. Cl.
*C11B 9/00* (2006.01)
*C07D 307/79* (2006.01)

(52) U.S. Cl.
CPC ............ *C11B 9/0076* (2013.01); *C07D 307/79* (2013.01)

(58) Field of Classification Search
CPC ........................... C07D 307/79; C11B 9/0076
USPC ............................ 512/13; 549/331, 429, 356
See application file for complete search history.

(56) References Cited

PUBLICATIONS

Sato et al. ("Metal-catalyzed organic photoreactions. Photoreactions of compounds containing a carbon-oxygen or carbon-nitrogen multiple bond with alcohols in the presence of titanium(IV) chloride or uranyl chloride", Bulletin of the Chemical Society of Japan, Dep. Appl. Chem., Waseda Univ., Tokyo, Japan, 1977, 50(10), pp. 2714-2730).*

* cited by examiner

*Primary Examiner* — Ling Choi
*Assistant Examiner* — Lanee Reuther
(74) *Attorney, Agent, or Firm* — XuFan Tseng; Martin Zhang; Elizabeth M. Quirk

(57) ABSTRACT

The present invention is directed to novel diethyl-methyl-hexahydro-isobenzofuran compounds and a method of improving, enhancing or modifying a fragrance formulation through the addition of an olfactory acceptable amount of these novel compounds.

18 Claims, No Drawings

DIETHYL-METHYL-HEXAHYDRO-ISOBENZOFURANS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

SUMMARY OF THE INVENTION

The present invention provides novel chemicals and their unexpected advantageous use in enhancing, improving or modifying the fragrance of perfumes, colognes, toilet waters, fabric care products, personal products and the like.

More specifically, the present invention is directed to novel diethyl-methyl-hexahydro-isobenzofuran compounds that exhibit unexpected powerful and complex fragrance effect, particularly woody, green, fresh and earthy combined with fruity and watery notes, and a method of improving, enhancing or modifying a fragrance formulation through the addition of an olfactory acceptable amount of diethyl-methyl-hexahydro-isobenzofurans represented by Formula I set forth below:

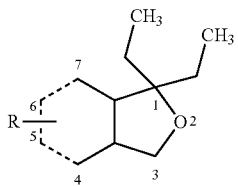

Formula I wherein the dashed lines represent a single bond or a double bond and only one double bond is present; and wherein R represents —$CH_3$ at 5 or 6 position.

These and other embodiments of the present invention will be apparent by reading the following specification.

DETAILED DESCRIPTION OF THE INVENTION

It is known to those with the skill in the art that Formula I as defined above provides the following novel compounds:

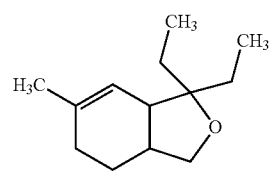

Formula II

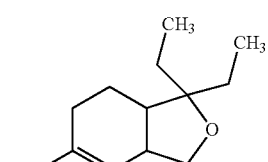

Formula III

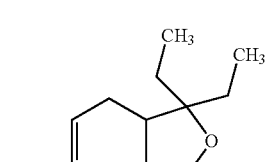

Formula IV

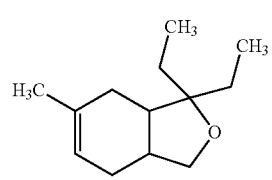

Formula V

Those with the skill in the art will recognize that

Formula II represents 1,1-diethyl-6-methyl-1,3,3a,4,5,7a-hexahydro-isobenzofuran;

Formula III represents 1,1-diethyl-5-methyl-1,3,3a,6,7,7a-hexahydro-isobenzofuran;

Formula IV represents 1,1-diethyl-5-methyl-1,3,3a,4,7,7a-hexahydro-isobenzofuran; and Formula V represents 1,1-diethyl-6-methyl-1,3,3a,4,7,7a-hexahydro-isobenzofuran.

The compounds of the present invention can be prepared from maleic anhydride and isoprene (both commercially available). The reaction steps can be depicted by the scheme shown as follows:

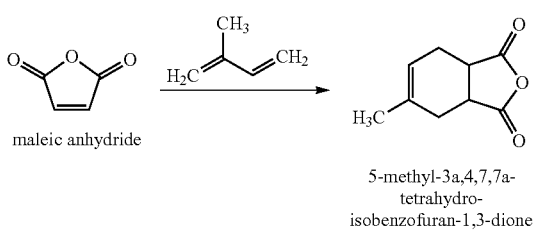

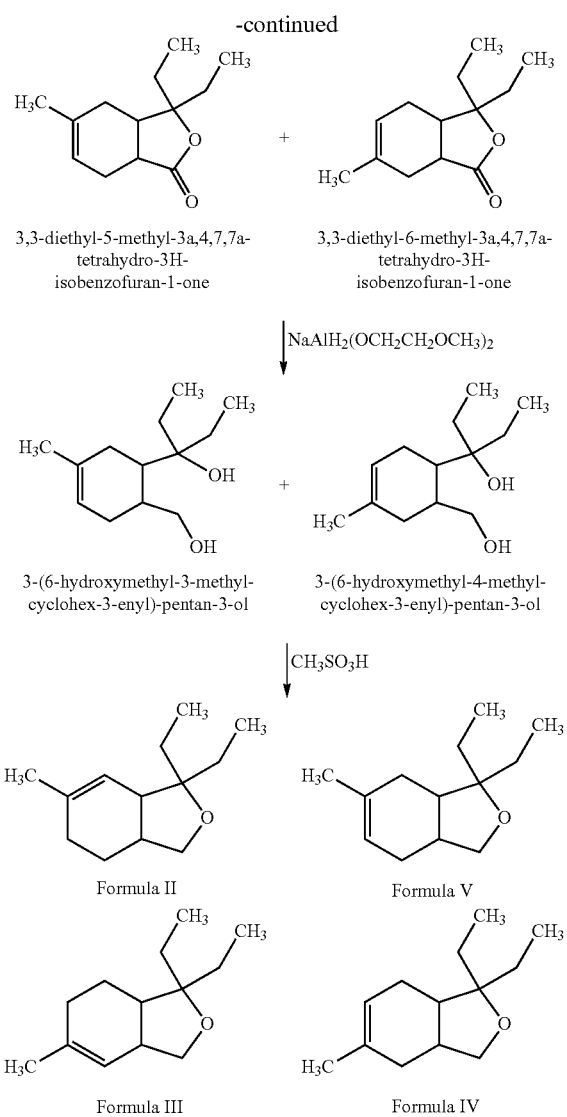

Those with skill in the art will recognize that the compounds of the present invention contain a number of positional and trans- and cis-isomers. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning products, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk; and flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), 2-ethyl-4-(2,2,3-trimethyl-3-cyclopenten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methylpentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention may comprise a compound of the present invention and further a complementary fragrance compound as defined above.

The term "fragrance product" means a consumer product that adds a fragrance or masks a malodor. Fragrance products may include, for example, perfumes, colognes, toilet water, personal care products such as soaps, shower gels, and hair care products, fabric care products, air fresheners, cosmetic products, and cleaning products such as detergents, dishwashing compositions, scrubbing compounds, and window cleaners. The fragrance product of the present invention is a consumer product that contains a compound of the present invention. The fragrance product of the present invention may contain a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 50 weight percent, preferably from 0.1 to about 25 weight percent, and more preferably from about 0.5 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation this ingredient provides powerful and complex fragrance effect, particularly woody, green, fresh and earthy combined with fruity and watery notes, which make the fragrance formulation more desirable and noticeable and add the perception of value. All of the odor qualities found in this material assist in beautifying and enhancing the finished accord improving the performance of the other materials in the fragrance. The fruity side is found in many fragrances today which happens to be very trendy, especially for the younger consumers.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, M is understood to be molar, L is understood to be liter, mL is understood to be milliliter, and g is understood to be gram. IFF as used in the examples is understood to mean International Flavors & Fragrances Inc., New York, N.Y., USA.

Example I

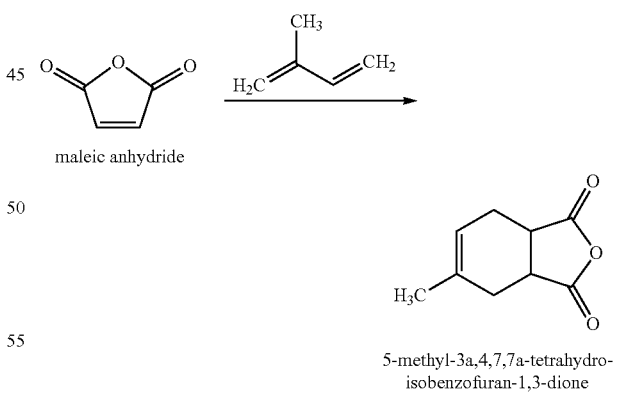

maleic anhydride 5-methyl-3a,4,7,7a-tetrahydro-isobenzofuran-1,3-dione

Preparation of 5-Methyl-3a,4,7,7a-tetrahydro-isobenzofuran-1,3-dione

A 5-L round bottom reaction flask fitted with a condenser was charged with maleic anhydride ($C_2H_2(CO)_2O$) (500 g) and tetrahydrofuran (THF) (3 L) and isoprene ($CH_2$=$C(CH_3)CH$=$CH_2$) (400 g) was then added at room temperature. The reaction was mildly exothermic. The reaction mixture was stirred at room temperature for about 2 hours till the Gas Chromatography ("GC") analysis showed the consumption of maleic anhydride. The resulting mixture containing crude 5-methyl-3a,4,7,7a-tetrahydro-isobenzofuran-1,3-dione was used directly in the next step.

Example II

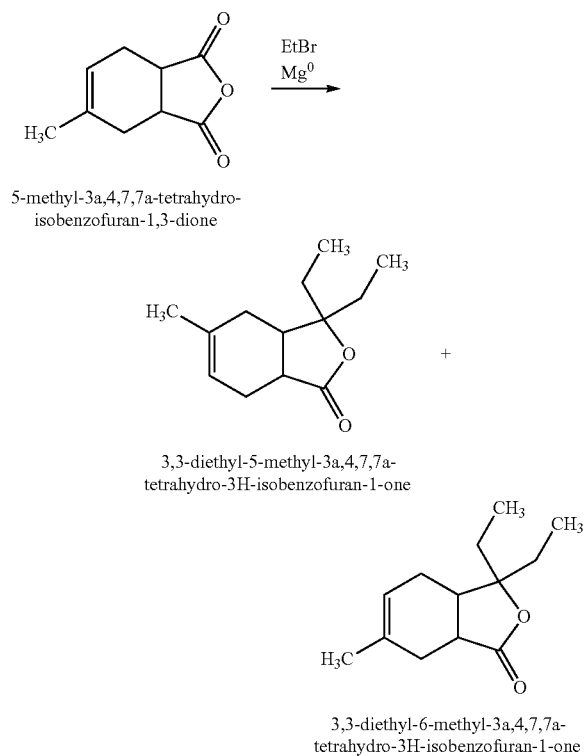

Preparation of 3,3-Diethyl-5-methyl-3a,4,7,7a-tetrahydro-3H-isobenzofuran-1-one and 3,3-Diethyl-6-methyl-3a,4,7,7a-tetrahydro-3H-isobenzofuran-1-one A 5-L round bottom reaction flask was charged with magnesium metal (Mg) (140 g) and THF (1 L) under nitrogen. Ethyl bromide (EtBr) (630 g) was fed into the reaction mixture dropwise while the temperature was maintained at 25° C. or below using a dry ice bath. After the feeding was completed, the reaction mixture was aged at room temperature for half an hour. Crude 5-methyl-3a,4,7,7a-tetrahydro-isobenzofuran-1,3-dione (1.7 L, ~56% of the mass of the resulting mixture obtained in EXAMPLE I) was then added dropwise while the temperature was maintained at 25° C. using a dry ice bath. The reaction mixture was consequently further aged at room temperature for another hour. The reaction mixture was poured into sulfuric acid ($H_2SO_4$) (10%) containing ice. Toluene was added. The organic and aqueous layers were shaken in a separatory funnel and separated. The aqueous layer was further washed with toluene. The organic layers were combined and washed with sodium carbonate ($Na_2CO_3$) solution until basic. The resulting solution was then distilled to afford 3,3-diethyl-5 or 6-methyl-3a,4,7,7a-tetrahydro-3H-isobenzofuran-1-one (457 g).

Example III

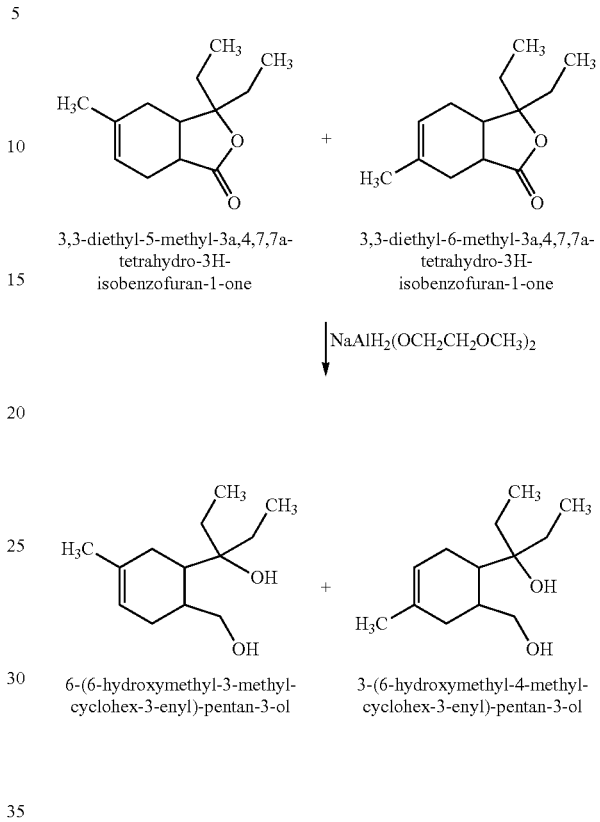

Preparation of 3-(6-Hydroxymethyl-3-methyl-cyclohex-3-enyl)-pentan-3-ol and 3-(6-Hydroxymethyl-4-methyl-cyclohex-3-enyl)-pentan-3-ol A 5-L round-bottom reaction flask was charged with Vitride® reducing agent (a solution of sodium bis(2-methoxyethoxy)aluminum dihydride ($NaAlH_2(OCH_2CH_2OCH_3)_2$) in toluene) (65%, 481 g) under a nitrogen atmosphere and heated to 85° C. 3,3-Diethyl-5 or 6-methyl-3a,4,7,7a-tetrahydro-3H-isobenzofuran-1-one (prepared as above in EXAMPLE II) (457 g) was fed in dropwise under nitrogen while the temperature was maintained at about 85° C. After 3,3-diethyl-5 or 6-methyl-3a,4,7,7a-tetrahydro-3H-isobenzofuran-1-one was consumed, the reaction mixture was aged at 85° C. for an hour, cooled to room temperature and quenched with isopropanol (100 mL). Sodium hydroxide (50%, 500 mL) was then added. The resulting mixture was heated to 50° C. with stirring, aged at 50° C. for an hour and cooled to room temperature. The organic and aqueous layers were shaken in a separatory funnel and separated in a separatory funnel. The organic layer was then distilled to remove toluene solvent and to azeotropically dry the solution to afford crude product 3-(6-hydroxymethyl-3 or 4-methyl-cyclohex-3-enyl)-pentan-3-ol.

Example IV

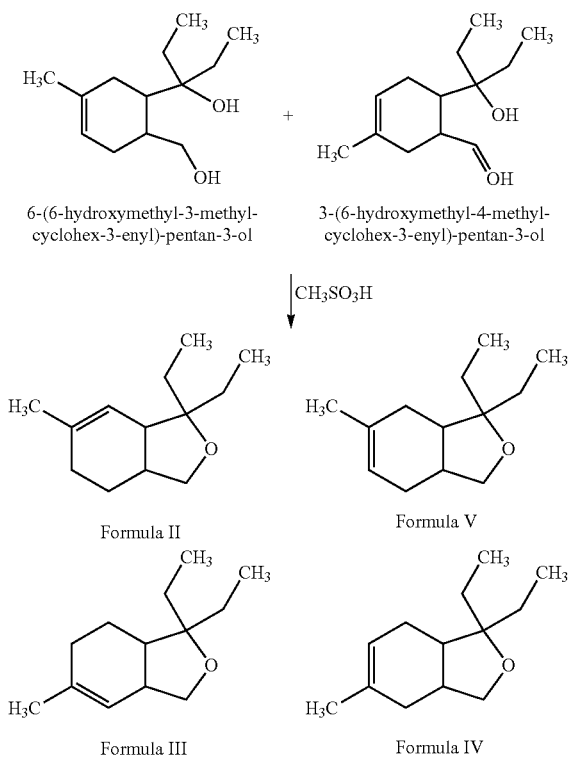

6-(6-hydroxymethyl-3-methyl-cyclohex-3-enyl)-pentan-3-ol 3-(6-hydroxymethyl-4-methyl-cyclohex-3-enyl)-pentan-3-ol Formula II Formula V Formula III Formula IV Preparation of 1,1-Diethyl-6-methyl-1,3,3a,4,5,7a-hexahydro-isobenzofuran (Formula II), 1,1-Diethyl-5-methyl-1,3,3a,6,7,7a-hexahydro-isobenzofuran (Formula III), 1,1-Diethyl-5-methyl-1,3,3a,4,7,7a-hexahydro-isobenzofuran (Formula IV) and 1,1-Diethyl-6-methyl-1,3,3a,4,7,7a-hexahydro-isobenzofuran (Formula V)

Crude 3-(6-hydroxymethyl-3 or 4-methyl-cyclohex-3-enyl)-pentan-3-ol (prepared as above in EXAMPLE III), toluene (750 mL) and methanesulfonic acid ($CH_3SO_3H$) (4.44 g) were charged into a 5 L round-bottom reaction flask fitted with a Bidwell-Sterling trap at room temperature. The reaction mixture was then heated to reflux and water was collected and removed via the Bidwell-Sterling trap. The reaction mixture was cooled to room temperature and transferred to a separatory funnel. The organic and aqueous layers were separated. The organic layer was washed with $Na_2CO_3$ solution until basic and then distilled to afford a mixture of 1,1-diethyl-6-methyl-1,3,3a,4,5,7a-hexahydro-isobenzofuran (Formula II), 1,1-diethyl-5-methyl-1,3,3a,6,7,7a-hexahydro-isobenzofuran (Formula III), 1,1-diethyl-5-methyl-1,3,3a,4,7,7a-hexahydro-isobenzofuran (Formula IV) and 1,1-diethyl-6-methyl-1,3,3a,4,7,7a-hexahydro-isobenzofuran (Formula V) (328 g). Individual isomers were then further separated and analyzed using preparative GC to afford 1,1-diethyl-6-methyl-1,3,3a,4,5,7a-hexahydro-isobenzofuran (Formula II) (39% by weight of the isomeric mixture), 1,1-diethyl-5-methyl-1,3,3a,6,7,7a-hexahydro-isobenzofuran (Formula III) (42%) and a mixture of 1,1-diethyl-5-methyl-1,3,3a,4,7,7a-hexahydro-isobenzofuran (Formula IV) and 1,1-diethyl-6-methyl-1,3,3a,4,7,7a-hexahydro-isobenzofuran (Formula V) (19%) (Formula IV:Formula V is about 1:1).

The isomeric mixture of Formula II-V prepared as above possessed the NMR spectral characteristics of:

$^1$H NMR (500 MHz, $CDCl_3$): 0.80-0.91 ppm (m, 6H), 1.36-1.55 ppm (m, 3H), 1.58-1.66 ppm (m, 1H), 1.66-1.69 ppm (2s, 3H), 1.76-2.28 ppm (m, 5H), 2.43-2.63 ppm (m, 1H), 3.31-3.58 ppm (m, 1H), 3.78-4.20 ppm (m, 1H), 5.26-5.44 ppm (m, 1H). Extra visible peaks for Formula IV and V: 0.90-1.00 ppm (m, 6H), 1.58-1.69 ppm (m, 2H), 1.70 ppm (br, 3H), 1.75-2.10 ppm (m, 4H), 2.20-2.50 ppm (m, 3H), 2.98-3.16 ppm (m, 1H), 5.42-5.50 ppm (m, 1H).

1,1-Diethyl-6-methyl-1,3,3a,4,5,7a-hexahydro-isobenzofuran (Formula II) possessed the NMR spectral characteristics of:

$^1$H NMR (500 MHz, $CDCl_3$): 5.25-5.28 ppm (m, 1H), 3.88 ppm (d, 1H, J=8.63 Hz, of d, J=6.73 Hz), 3.55 ppm (d, 1H, J=8.60 Hz, of d, J=4.60 Hz), 2.46-2.49 ppm (m, 1H), 2.33-2.40 ppm (m, 1H), 1.87-1.92 ppm (m, 2H), 1.70 ppm (s, 3H), 1.35-1.69 ppm (m, 6H), 0.88 ppm (t, 3H, J=7.43 Hz), 0.87 ppm (t, 3H, J=7.53 Hz).

1,1-Diethyl-6-methyl-1,3,3a,4,5,7a-hexahydro-isobenzofuran was described as having fresh, herbal and woody notes.

1,1-Diethyl-5-methyl-1,3,3a,6,7,7a-hexahydro-isobenzofuran (Formula III) possessed the NMR spectral characteristics of:

$^1$H NMR (500 MHz, $CDCl_3$): 5.33 ppm (s, 1H), 3.95 ppm (t, 1H, J=8.23 Hz), 3.42 ppm (d, 1H, J=9.88 Hz, of d, J=7.93 Hz), 2.89 ppm (br. s, 1H), 1.91-2.02 ppm (m, 2H), 1.83-1.89 ppm (m, 1H), 1.68 ppm (s, 3H), 1.54-1.67 ppm (m, 3H), 1.37-1.52 ppm (m, 3H), 0.88 ppm (t, 3H, J=7.45 Hz), 0.84 ppm (t, 3H, J=7.50 Hz).

1,1-Diethyl-5-methyl-1,3,3a,6,7,7a-hexahydro-isobenzofuran was described as having very sweet and floral notes.

The mixture of 1,1-diethyl-5-methyl-1,3,3a,4,7,7a-hexahydro-isobenzofuran (Formula IV) and 1,1-diethyl-6-methyl-1,3,3a,4,7,7a-hexahydro-isobenzofuran (Formula V) possessed the NMR spectral characteristics of:

$^1$H NMR (400 MHz, $CDCl_3$): 5.44 ppm (s, ~48.2% of 1H), 5.38 ppm (s, ~51.8% of 1H), 3.81-3.88 ppm (m, 1H), 3.48-3.54 ppm (m, 1H), 2.08-2.62 ppm (m, 3H), 1.75-2.07 ppm (m, 3H), 1.66 & 1.69 ppm (2s, 3H), 1.58-1.65 ppm (m, 1H), 1.39-1.52 ppm (m, 3H), 0.81-0.90 ppm (m, 6H).

The mixture of 1,1-diethyl-5-methyl-1,3,3a,4,7,7a-hexahydro-isobenzofuran and 1,1-diethyl-6-methyl-1,3,3a,4,7,7a-hexahydro-isobenzofuran was described as having sweet, herbal and citrus notes.

Example V

The following analogs were prepared similarly according to EXAMPLE I-IV.

Preparation of 1,1-Diethyl-4-methyl-1,3,3a,4,7,7a-hexahydro-isobenzofuran (Formula VIa), 1,1-Diethyl-4-methyl-1,3,3a,6,7,7a-hexahydro-isobenzofuran (Formula VIb), 1,1-Diethyl-7-methyl-1,3,3a,4,7,7a-hexahydro-isobenzofuran (Formula VIIa) and 1,1-Diethyl-7-methyl-1,3,3a,4,5,7a-hexahydro-isobenzofuran (Formula VIIb)

A mixture of Formula VI 1,1-diethyl-4-methyl-1,3,3a,4 or 6,7,7a-hexahydro-isobenzofuran including Formula VIa and VIb and Formula VII 1,1-diethyl-7-methyl-1,3,3a,4,5 or 7,7a-hexahydro-isobenzofuran including Formula VIIa and VIIb was prepared. Formula VI and Formula VII had a weight ratio of about 70:30.

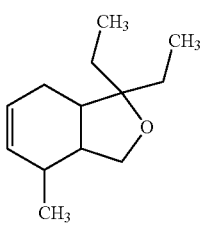
Formula VIa

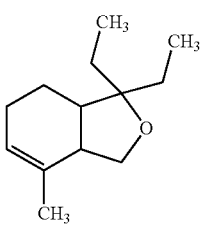
Formula VIb

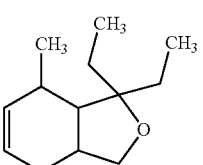
Formula VIIa

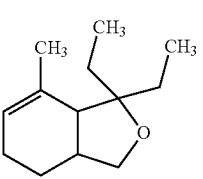
Formula VIIb

The mixture of Formula VI and VII obtained in the above preparation possessed the NMR spectral characteristics of:

$^1$H NMR (500 MHz, CDCl$_3$): 5.60-5.76 ppm (m, 1H), 5.35-5.51 ppm (m, 1H), 3.76-3.87 ppm (m, 1H), 3.48-3.57 ppm (m, 1H), 1.93-2.98 ppm (m, 5H), 1.55-1.79 ppm (m, 2H), 1.41-1.54 ppm (m, 2H), 0.90-0.98 ppm (m, 3H), 0.78-0.90 ppm (m, 6H).

The mixture of Formula VI and VII was described as having woody and earthy notes with galbanum, cypress and eucalyptus characters.

Preparation of 1,1-Diethyl-5-methyl-octahydro-isobenzofuran (Formula VIII) and 1,1-Diethyl-6-methyl-octahydro-isobenzofuran (Formula IX)

The isomeric mixture of Formula II-V prepared as above was subsequently subjected to hydrogen gas in the presence of palladium on carbon to afford 1,1-diethyl-5-methyl-octahydro-isobenzofuran (Formula VIII) and 1,1-diethyl-6-methyl-octahydro-isobenzofuran (Formula IX). Formula VIII and Formula IX had a weight ratio of about 50:50.

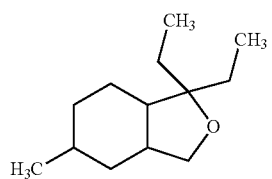
Formula VIII

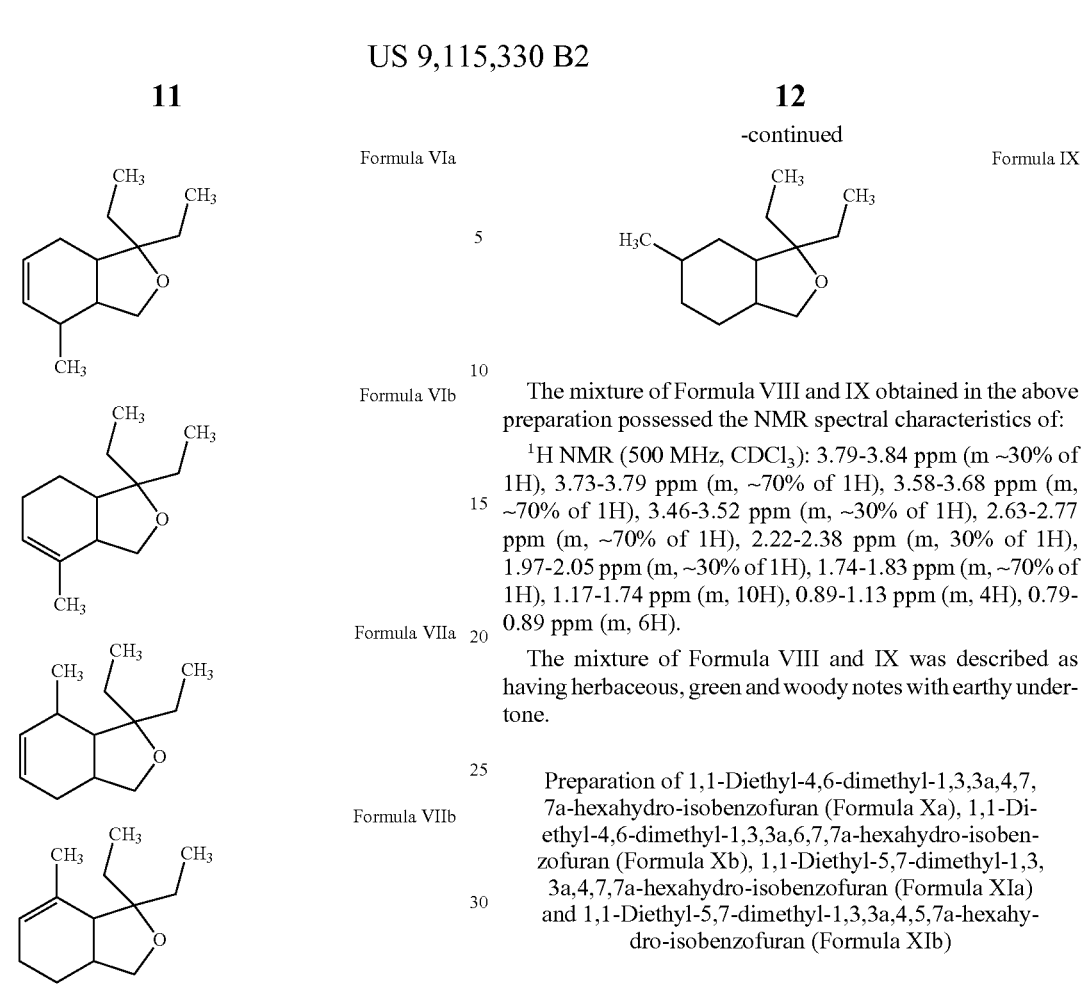

The mixture of Formula VIII and IX obtained in the above preparation possessed the NMR spectral characteristics of:

$^1$H NMR (500 MHz, CDCl$_3$): 3.79-3.84 ppm (m ~30% of 1H), 3.73-3.79 ppm (m, ~70% of 1H), 3.58-3.68 ppm (m, ~70% of 1H), 3.46-3.52 ppm (m, ~30% of 1H), 2.63-2.77 ppm (m, ~70% of 1H), 2.22-2.38 ppm (m, 30% of 1H), 1.97-2.05 ppm (m, ~30% of 1H), 1.74-1.83 ppm (m, ~70% of 1H), 1.17-1.74 ppm (m, 10H), 0.89-1.13 ppm (m, 4H), 0.79-0.89 ppm (m, 6H).

The mixture of Formula VIII and IX was described as having herbaceous, green and woody notes with earthy undertone.

Preparation of 1,1-Diethyl-4,6-dimethyl-1,3,3a,4,7,7a-hexahydro-isobenzofuran (Formula Xa), 1,1-Diethyl-4,6-dimethyl-1,3,3a,6,7,7a-hexahydro-isobenzofuran (Formula Xb), 1,1-Diethyl-5,7-dimethyl-1,3,3a,4,7,7a-hexahydro-isobenzofuran (Formula XIa) and 1,1-Diethyl-5,7-dimethyl-1,3,3a,4,5,7a-hexahydro-isobenzofuran (Formula XIb)

A mixture of Formula X 1,1-diethyl-4,6-dimethyl-1,3,3a,4 or 6,7,7a-hexahydro-isobenzofuran including Formula Xa and Xb and Formula XI 1,1-diethyl-5,7-dimethyl-1,3,3a,4,5 or 7,a-hexahydro-isobenzofuran including Formula XIa and XIb was prepared. Formula X and Formula XI had a weight ratio of about 80:20.

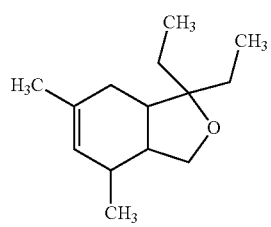
Formula Xa

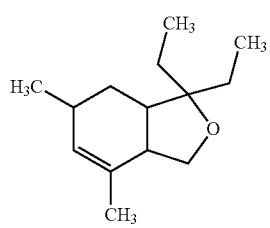
Formula Xb

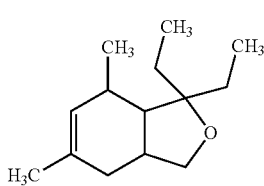
Formula XIa

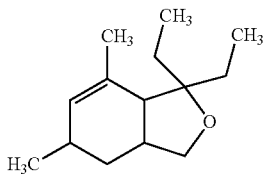

Formula XIb

The mixture of Formula X and XI obtained in the above preparation possessed the NMR spectral characteristics of:

$^1$H NMR (500 MHz, CDCl$_3$): 5.11-5.89 ppm (m, 1H), 2.89-4.06 ppm (m, 2H), 2.50 & 2.59 ppm (2s, 1H), 1.80-2.41 ppm (m, 2H), 1.62-1.79 ppm (m, 5H), 1.19-1.62 ppm (m, 4H), 0.82-1.17 ppm (m, 9H).

The mixture of Formula X and XI was described as having woody and spicy notes with leather-like quality, weak with little complexity.

Preparation of 1,1-Diethyl-3a,5-dimethyl-1,3,3a,4,7,7a-hexahydro-isobenzofuran (Formula XIIa), 1,1-Diethyl-3a,5-dimethyl-1,3,3a,6,7,7a-hexahydro-isobenzofuran (Formula XIIb), 1,1-Diethyl-3a,6-dimethyl-1,3,3a,4,7,7a-hexahydro-isobenzofuran (Formula XIIIa) and 1,1-Diethyl-3a,6-dimethyl-1,3,3a,4,5,7a-hexahydro-isobenzofuran (Formula XIIIb)

A mixture of Formula XII 1,1-diethyl-3a,5-dimethyl-1,3,3a,4 or 6,7,7a-hexahydro-isobenzofuran including Formula XIIa and XIIb and Formula XIII 1,1-diethyl-3a,6-dimethyl-1,3,3a,4,5 or 7,7a-hexahydro-isobenzofuran including Formula XIIIa and XIIIb was prepared. Formula XII and Formula XIII had a weight ratio of about 80:20.

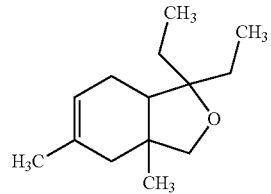

Formula XIIa

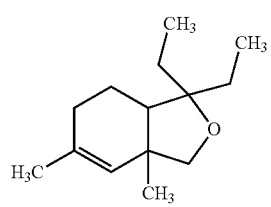

Formula XIIb

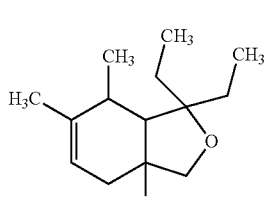

Formula XIIIa

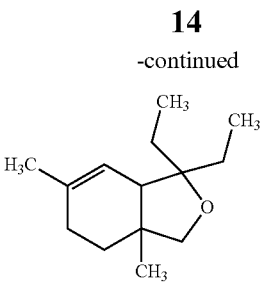

Formula XIIIb

The mixture of Formula XII and XIII obtained in the above preparation possessed the NMR spectral characteristics of:

$^1$H NMR (400 MHz, CDCl$_3$): 5.43 ppm (s, ~80% of 1H), 5.17 ppm (s, ~20% of 1H), 3.49-3.53 ppm (m, ~80% of 1H+~20% of 2H), 3.39 ppm (d, ~80% of 1H, J=8.02 Hz, of d, J=4.62 Hz), 1.25-2.28 ppm (m, 12H), 0.96-0.99 ppm (m, 3H), 0.80-0.89 ppm (m, 6H).

The mixture of Formula XII and XIII was described as having weak woody, floral, fruity and spicy notes with herbaceous background.

Preparation of 1,1,5-Trimethyl-1,3,3a,4,7,7a-hexahydro-isobenzofuran (Formula XIVa), 1,1,5-Trimethyl-1,3,3a,6,7,7a-hexahydro-isobenzofuran (Formula XIVb), 1,1,6-Trimethyl-1,3,3a,4,7,7a-hexahydro-isobenzofuran (Formula XVa) and 1,1,6-Trimethyl-1,3,3a,4,5,7a-hexahydro-isobenzofuran (Formula XVb)

A mixture of Formula XIV 1,1,5-trimethyl-1,3,3a,4 or 6,7,7a-hexahydro-isobenzofuran including Formula XIVa and XIVb and Formula XV 1,1,6-trimethyl-1,3,3a,4,5 or 7,7a-hexahydro-isobenzofuran including Formula XVa and XVb was prepared. Formula XIV and Formula XV had a weight ratio of about 50:50.

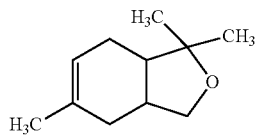

Formula XIVa

Formula XIVb

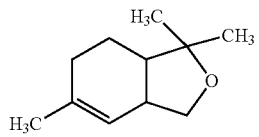

Formula XVa

Formula XVb

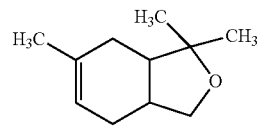

The mixture of Formula XIV and XV obtained in the above preparation possessed the NMR spectral characteristics of:

$^1$H NMR (500 MHz, CDCl$_3$): 5.34 ppm (s, ~54% of 1H), 5.28 ppm (s, ~46% of 1H), 4.00 ppm (t, ~54% of 1H, J=8.23 Hz), 3.95 ppm (t, ~46% of 1H, J=7.85 Hz), 3.56 ppm (d, ~54% of 1H, J=8.60 Hz, of d, J=4.60 Hz), 3.44 ppm (d, ~46% of 1H, J=9.40 Hz, of d, J=8.15 Hz), 1.76-2.59 ppm (m, 4H), 1.71 ppm (s, ~46% of 3H), 1.68 ppm (s, ~54% of 3H), 1.66-1.74 ppm (m, 1H), 1.49-1.57 ppm (m, ~46% of 1H), 1.36-1.46 ppm (m, ~54% of 1H), 1.26 ppm (s, ~46% of 3H), 1.22 ppm (s, ~54% of 6H), 1.09 ppm (~46% of 3H).

The mixture of Formula XIV and XV was described as having woody but mushroom-like and musty notes with earthy and herbaceous characters.

Preparation of 1,1,4-Trimethyl-1,3,3a,4,7,7a-hexahydro-isobenzofuran (Formula XVIa) and 1,1,4-Trimethyl-1,3,3a,6,7,7a-hexahydro-isobenzofuran (Formula XVIb)

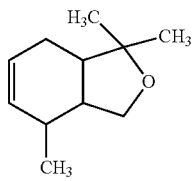

Formula XVIa

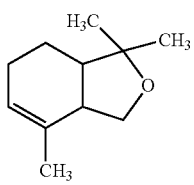

Formula XVIb

Formula XVI 1,1,4-trimethyl-1,3,3a,4 or 6,7,7a-hexahydro-isobenzofuran including Formula XVIa and XVIb obtained in the above preparation possessed the NMR spectral characteristics of:

$^1$H NMR (500 MHz, CDCl$_3$): 5.64-5.69 ppm (m, 1H), 5.57 ppm (d, ~28% of 1H, J=10.15 Hz), 5.46 ppm (d, ~72% of 1H, J=9.95 Hz), 3.83 ppm (t, 1H, J=7.93 Hz), 3.54 ppm (d, 1H, J=11.03 Hz, of d, J=8.08 Hz), 2.81-2.88 ppm (~72% of 1H), 2.72 ppm (s, ~28% of 1H), 2.55 ppm (s, ~72% of 1H), 2.41 ppm (t, ~28% of 1H, J=6.60 Hz), 1.91-2.29 ppm (m, 3H), 1.31 ppm (s, ~28% of 3H), 1.24 ppm (s, ~72% of 3H), 1.22 ppm (s, ~72% of 3H), 1.19 ppm (s, ~28% of 3H), 1.16 ppm (d, ~28% of 3H, J=7.80 Hz), 0.95 ppm (d, ~72% of 3H, J=7.45 Hz).

Formula XVI was described as having fresh, earthy, camphoraceous and piney notes with solvent "kerosene"-like and mushroom-like characters.

Preparation of 1,1,5,7-Tetramethyl-1,3,3a,4,7,7a-hexahydro-isobenzofuran (Formula XVIIa) and 1,1,5,7-Tetramethyl-1,3,3a,4,5,7a-hexahydro-isobenzofuran (XVIIb)

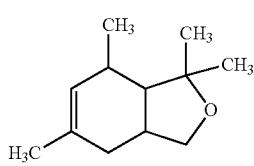

Formula XVIIa

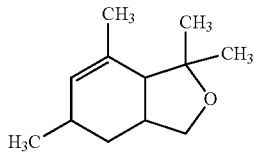

Formula XVIIb

Formula XVII 1,1,5,7-tetramethyl-1,3,3a,4,5 or 7,7a-hexahydro-isobenzofuran including Formula XVIIa and XVIIb obtained in the above preparation possessed the NMR spectral characteristics of:

$^1$H NMR (500 MHz, CDCl$_3$): 5.12-5.36 ppm (m, 1H), 3.77-3.88 ppm (m, 1H), 3.48-3.63 ppm (m, 1H), 2.67-2.83 ppm (m, 1H), 2.37-2.57 ppm (m, 1H), 1.89-2.10 ppm (m, 2H), 1.71-1.88 ppm (m, 1H), 1.64-1.69 ppm (m, 3H), 1.09-1.32 ppm (m, 6H), 0.91-1.07 ppm (m, 3H).

Formula XVII was described as having fresh, herbaceous, green and woody notes with galbanum character.

Preparation of 1,1,3a,4,6-Pentamethyl-1,3,3a,4,7,7a-hexahydro-isobenzofuran (Formula XVIIIa) and 1,1,3a,4,6-Pentamethyl-1,3,3a,6,7,7a-hexahydro-isobenzofuran (Formula XVIIIb)

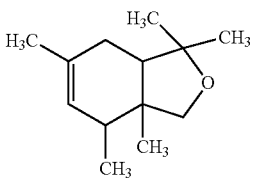

Formula XVIIIa

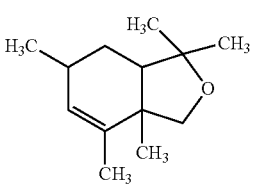

Formula XVIIIb

Formula XVIII 1,1,3a,4,6-pentamethyl-1,3,3a,4 or 6,7,7a-hexahydro-isobenzofuran including Formula XVIIIa and XVIIIb obtained in the above preparation possessed the NMR spectral characteristics of:

$^1$H NMR (400 MHz, CDCl$_3$): 5.26 ppm (s, 1H), 3.46 ppm (d, 1H, J=8.80 Hz), 3.33 (d, 1H, J=8.72 Hz), 2.00-2.08 ppm (m, 1H), 1.83-1.97 ppm (m, 2H), 1.74-1.77 ppm (m, 3H), 1.65-1.74 ppm (m, 1H), 1.28 ppm (s, 3H), 1.21 ppm (s, 3H), 1.04 ppm (s, 3H), 0.98 ppm (d, 3H, J=7.36 Hz).

Formula XVIII was described as having woody, fresh and herbaceous notes with menthol-like background.

Preparation of 5-Methyl-1,1-dipropyl-1,3,3a,4,7,7a-hexahydro-isobenzofuran (Formula XIXa), 5-Methyl-1,1-dipropyl-1,3,3a,6,7,7a-hexahydro-isobenzofuran (Formula XIXb), 6-Methyl-1,1-dipropyl-1,3,3a,4,7,7a-hexahydro-isobenzofuran (Formula XXa) and 6-Methyl-1,1-dipropyl-1,3,3a,4,5,7a-hexahydro-isobenzofuran (Formula XXb)

A mixture of Formula XIX 5-methyl-1,1-dipropyl-1,3,3a,4 or 6,7,7a-hexahydro-isobenzofuran including Formula XIXa and XIXb and Formula XX 6-methyl-1,1-dipropyl-1,3,3a,4,5 or 7,7a-hexahydro-isobenzofuran including Formula XXa and XXb was prepared. Formula XIX and Formula XX had a weight ratio of about 50:50.

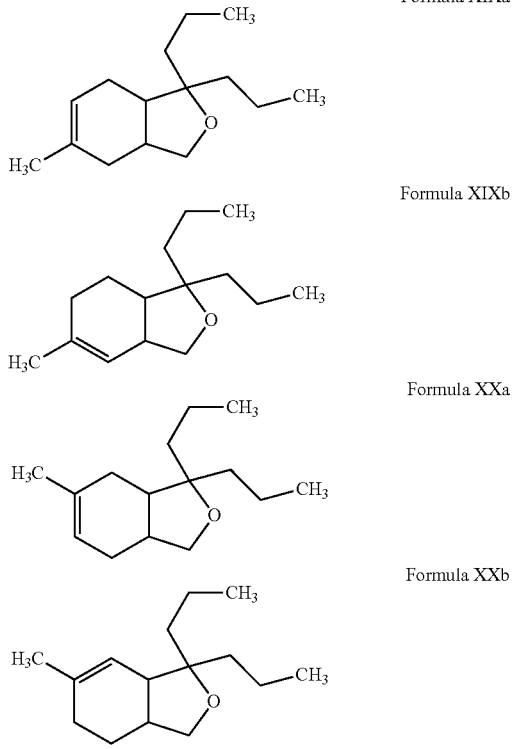

The mixture of Formula XIX and XX obtained in the above preparation possessed the NMR spectral characteristics of:
$^1$H NMR (500 MHz, CDCl$_3$): 5.43-5.45 ppm (m, ~50% of 1H), 5.36-5.38 ppm (m, ~50% of 1H), 3.80-3.89 ppm (m, 1H), 3.46-3.57 ppm (m, 1H), 2.18-2.63 ppm (m, 2H), 1.76-2.14 ppm (m, 4H), 1.52-1.62 ppm (m, 2H), 1.36-1.47 ppm (m, 4H), 1.20-1.36 ppm (m, 4H), 0.88-0.93 ppm (m, 6H).

The mixture of Formula XIX and XX was described as having fruity but very weak note with sour character.

Preparation of
3,3-Diethyl-4-oxa-tricyclo[5.2.1.0*2,6]-decane
(Formula XXI)

Cyclopentadiene was used as a starting material and an additional hydrogenation step was carried out to obtain 3,3-diethyl-4-oxa-tricyclo[5.2.1.0*2,6]-decane.

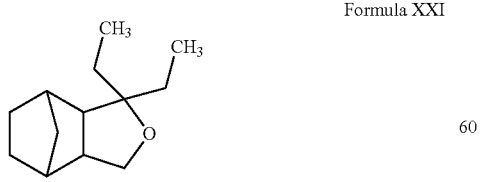

$^1$H NMR (500 MHz, CDCl$_3$): 3.78 ppm (d, 1H, J=9.83 Hz, of d, J=2.08 Hz), 3.53 ppm (d, 1H, J=9.58 Hz, of d, J=8.13 Hz), 2.59-2.65 ppm (m, 1H), 2.24 ppm (s, 1H), 2.20 ppm (s, 1H), 2.08 ppm (d, 1H, J=10.18 Hz, of d, J=3.28 Hz), 1.87- 1.94 ppm (m, 1H), 1.71-1.82 ppm (m, 2H), 1.63-1.71 ppm (m, 1H), 1.38-1.48 ppm (m, 3H), 1.24-1.38 ppm (m, 3H), 0.91 ppm (t, 3H, J=7.60 Hz), 0.77 ppm (t, 3H, J=7.40 Hz).

3,3-Diethyl-4-oxa-tricyclo[5.2.1.0*2,6*]-decane (Formula XXI) was described as having camphoraceous character with earthy and animalic undertones, herbaceous, piney and musty notes but weak.

Preparation of 1-Ethyl-3a,4,6-trimethyl-1,3,3a,4,7, 7a-hexahydro-isobenzofuran (Formula XXIIa), 1-Ethyl-3a,4,6-trimethyl-1,3,3a,6,7,7a-hexahydro-isobenzofuran (Formula XXIIb), 1-Ethyl-5,7,7a-trimethyl-1,3,3a,4,7,7a-hexahydro-isobenzofuran (Formula XXIIIa) and 1-Ethyl-5,7,7a-trimethyl-1,3, 3a,4,5,7a-hexahydro-isobenzofuran (Formula XXIIIb)

A mixture of Formula XXII 1-ethyl-3a,4,6-trimethyl-1,3, 3a,4 or 6,7,7a-hexahydro-isobenzofuran including Formula XXIIa and XXIIb and Formula XXIII 1-ethyl-5,7,7a-trimethyl-1,3,3a,4,5 or 7,7a-hexahydro-isobenzofuran including Formula XXIIIa and XXIIIb was prepared. Formula XXII and Formula XXIII had a weight ratio of about 70:30.

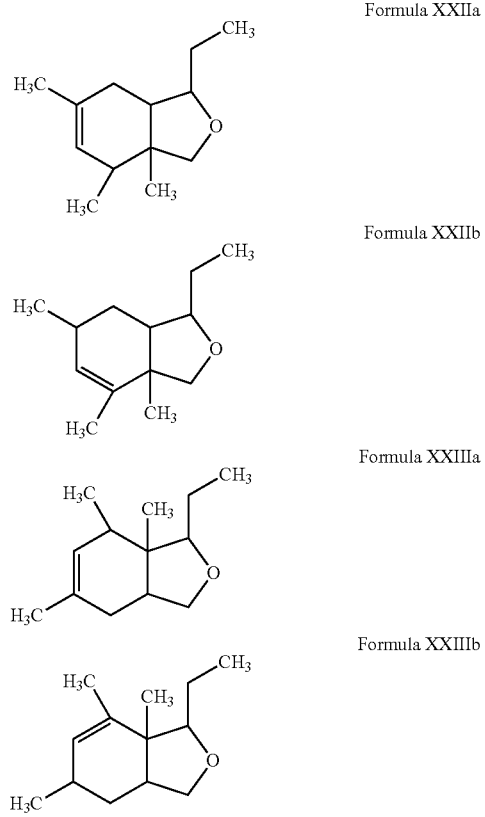

The mixture of Formula XXII and XXIII obtained in the above preparation possessed the NMR spectral characteristics of:
$^1$H NMR (400 MHz, CDCl$_3$): 5.30-5.33 ppm (m, ~67% of 1H), 5.22-5.24 ppm (m, ~33% of 1H), 3.30-4.14 ppm (m, 3H), 1.72-2.23 ppm (m, 3H), 1.69 ppm (s, 3H), 1.45-1.68 ppm (m, 3H), 1.21 ppm (s, ~100% of 3H of XIII), 0.86-1.02 ppm (m, 100% of 9H of XII+100% of 6H of XIII).

The mixture of Formula XXII and XXIII was described as having woody, camphoraceous but dirty notes with piney and slightly animalic aspect.

Example VI

The fragrance properties of the above compounds (i.e., Formula II-XXIII) were evaluated using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Chemical Name | Compound | Odor Profile | Strength | Complexity |
|---|---|---|---|---|
| 1,1-Diethyl-6-methyl-1,3,3a,4,5,7a-hexahydro-isobenzofuran; 1,1-Diethyl-5-methyl-1,3,3a,6,7,7a-hexahydro-isobenzofuran; 1,1-Diethyl-5-methyl-1,3,3a,4,7,7a-hexahydro-isobenzofuran and 1,1-Diethyl-6-methyl-1,3,3a,4,7,7a-hexahydro-isobenzofuran (Formula II-V) | [structures] | Woody, green, fresh and earthy notes with herbaceous and tomato leaf background, further combined with fruity and watery notes. | 9.5 | 9 |
| 1,1-Diethyl-4-methyl-1,3,3a,4 or 6,7,7a-hexahydro-isobenzofuran and 1,1-Diethyl-7-methyl-1,3,3a,4,5 or 7,7a-hexahydro-isobenzofuran (Formula VI and VII) | [structures] | Woody and earthy notes with galbanum, cypress and eucalyptus characters. | 7.5 | 7 |

-continued

| Chemical Name | Compound | Odor Profile | Strength | Complexity |
|---|---|---|---|---|
| 1,1-Diethyl-5 or 6-methyl-octahydro-isobenzofuran (Formula VIII and IX) | | Herbaceous, green and woody notes with earthy undertone. | 6 | 6 |
| 1,1-Diethyl-4,6-dimethyl-1,3,3a,4 or 6,7,7a-hexahydro-isobenzofuran and 1,1-Diethyl-5,7-dimethyl-1,3,3a,4,5 or 7,7a-hexahydro-isobenzofuran (Formula X and XI) | | Woody and spicy notes with leather-like quality, weak with little complexity. | 4 | 4 |

-continued

| Chemical Name | Compound | Odor Profile | Strength | Complexity |
|---|---|---|---|---|
| 1,1-Diethyl-3a,5-dimethyl-1,3,3a,4 or 6,7,7a-hexahydro-isobenzofuran and 1,1-Diethyl-3a,6-dimethyl-1,3,3a,4,5 or 7,7a-hexahydro-isobenzofuran (Formula XII and XIII) | | Weak woody, floral, fruity and spicy notes with herbaceous background. | 4 | 6 |
| 1,1,5-Trimethyl-1,3,3a,4 or 6,7,7a-hexahydro-isobenzofuran and 1,1,6-Trimethyl-1,3,3a,4,5 or 7,7a-hexahydro-isobenzofuran (Formula XIV and XV) | | Woody but mushroom-like and musty notes with earthy and herbaceous characters. | 5 | 4 |

| Chemical Name | Compound | Odor Profile | Strength | Complexity |
|---|---|---|---|---|
| 1,1,4-Trimethyl-1,3,3a,4 or 6,7,7a-hexahydro-isobenzofuran (Formula XVI) | 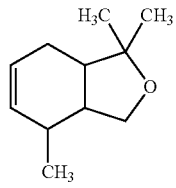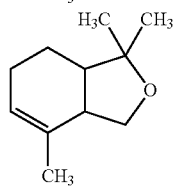 | Fresh, earthy, camphoraceous and piney notes with solvent "kerosene"-like and mushroom-like characters. | 7.5 | 7 |
| 1,1,5,7-Tetramethyl-1,3,3a,4,5 or 7,7a-hexahydro-isobenzofuran (Formula XVII) | 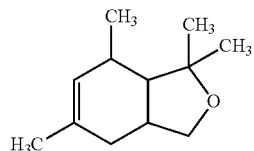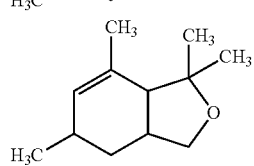 | Fresh, herbaceous, green and woody notes with galbanum character. | 8 | 8 |
| 1,1,3a,4,6-Pentamethyl-1,3,3a,4 or 6,7,7a hexahydro-isobenzofuran (Formula XVIII) | 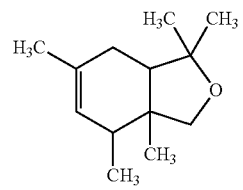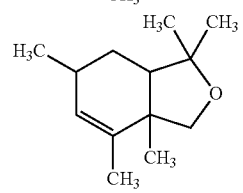 | Woody, fresh and herbaceous notes with menthol-like background. | 6 | 5 |

-continued

| Chemical Name | Compound | Odor Profile | Strength | Complexity |
|---|---|---|---|---|
| 5-Methyl-1,1-dipropyl-1,3,3a,4 or 6,7,7a-hexahydro-isobenzofuran and 6-Methy1-1,1-dipropyl-1,3,3a,4,5 or 7,7a-hexahydro-isobenzofuran (Formula XIX and XX) | | Fruity but very weak note with sour character. | 1 | 1 |
| 3,3-Diethyl-4-oxa-tricyclo[5.2.1.0*2,6*]-decane (Formula XXI) | | Camphoraceous character with earthy and animalic undertones. Herbaceous, piney and musty notes but weak. | 3 | 3 |
| 1-Ethyl-3a,4,6-trimethyl-1,3,3a,4 or 6,7,7a-hexahydro-isobenzofuran and 1-Ethyl-5,7,7a-trimethyl-1,3,3a,4,5 or 7,7a-hexahydro-isobenzofuran (Formula XXII and XXIII) | | Woody, camphoraceous but dirty notes with piney and slightly animalic aspect. | 4 | 4 |

Among the compounds described above (i.e., Formula II-XXIII), no structure and fragrance activity relationships could be established. However, the mixture of Formula II-V exhibited particularly desirable, strong, and complex odors, superior to all other analogs. Such advantageous properties were found to be unexpected and unpredictable.

What is claimed is:

1. A mixture of 1,1-diethyl-5-methyl-1,3,3a,4,7,7a-hexahydro-isobenzofuran and 1,1-diethyl-6-methyl-1,3,3a,4,7,7a-hexahydro-isobenzofuran.

2. A fragrance formulation containing an olfactory acceptable amount of
the mixture of claim 1.

3. The fragrance formulation of claim 2, wherein the olfactory acceptable amount is from about 0.005 to about 50 weight percent of the fragrance formulation.

4. The fragrance formulation of claim 2, wherein the olfactory acceptable amount is from about 0.1 to about 25 weight percent of the fragrance formulation.

5. The fragrance formulation of claim 2, wherein the olfactory acceptable amount is from about 0.5 to about 10 weight percent of the fragrance formulation.

6. A method of improving, enhancing or modifying a fragrance formulation through the addition of an olfactory acceptable amount of
the mixture of claim 1.

7. A fragrance product containing an olfactory acceptable amount of the mixture of claim 1.

8. The fragrance product of claim 7, wherein the fragrance product is selected from the group consisting of a perfume, a cologne, toilet water, a cosmetic product, a personal care product, a fabric care product, a cleaning product and an air freshener.

9. The fragrance product of claim 8, wherein the cleaning product is selected from the group consisting of a detergent, a dishwashing composition, a scrubbing compound and a window cleaner.

10. A mixture of 1,1-diethyl-6-methyl-1,3,3a,4,5,7a-hexahydro-isobenzofuran, 1,1-diethyl-5-methyl-1,3,3a,6,7,7a-hexahydro-isobenzofuran, 1,1-diethyl-5-methyl-1,3,3a,4,7,7a-hexahydro-isobenzofuran and 1,1-diethyl-6-methyl-1,3,3a,4,7,7a-hexahydro-isobenzofuran.

11. A fragrance formulation containing an olfactory acceptable amount of the mixture of claim 10.

12. The fragrance formulation of claim 11, wherein the olfactory acceptable amount is from about 0.005 to about 50 weight percent of the fragrance formulation.

13. The fragrance formulation of claim 11, wherein the olfactory acceptable amount is from about 0.1 to about 25 weight percent of the fragrance formulation.

14. The fragrance formulation of claim 11, wherein the olfactory acceptable amount is from about 0.5 to about 10 weight percent of the fragrance formulation.

15. A fragrance product containing an olfactory acceptable amount of the mixture of claim 10.

16. The fragrance product of claim 15, wherein the fragrance product is selected from the group consisting of a perfume, a cologne, toilet water, a cosmetic product, a personal care product, a fabric care product, a cleaning product and an air freshener.

17. The fragrance product of claim 16, wherein the cleaning product is selected from the group consisting of a detergent, a dishwashing composition, a scrubbing compound and a window cleaner.

18. A method of improving, enhancing or modifying a fragrance formulation through the addition of an olfactory acceptable amount of a mixture of 1,1-diethyl-6-methyl-1,3,3a,4,5,7a-hexahydro-isobenzofuran, 1,1-diethyl-5-methyl-1,3,3a,6,7,7a-hexahydro-isobenzofuran, 1,1-diethyl-5-methyl-1,3,3a,4,7,7a-hexahydro-isobenzofuran and 1,1-diethyl-6-methyl-1,3,3a,4,7,7a-hexahydro-isobenzofuran.

* * * * *